United States Patent [19]
Wolff et al.

[11] Patent Number: 4,835,094
[45] Date of Patent: May 30, 1989

[54] COLOR PHOTOGRAPHIC RECORDING MATERIAL CONTAINING A COLOR COUPLER OF THE PYRAZOLOAZOLE SERIES

[75] Inventors: Erich Wolff, Solingen; Hans-Joachim Schumann, Cologne, both of Fed. Rep. of Germany

[73] Assignee: Agfa-Gevaert Aktiengesellschaft, Leverkusen, Fed. Rep. of Germany

[21] Appl. No.: 103,357

[22] Filed: Sep. 30, 1987

[30] Foreign Application Priority Data

Oct. 1, 1986 [DE] Fed. Rep. of Germany ....... 3633364

[51] Int. Cl.$^4$ ................................................ G03C 7/38
[52] U.S. Cl. ..................................... 430/558; 430/387
[58] Field of Search ................... 430/558 R, 543, 546, 430/387

[56] References Cited

U.S. PATENT DOCUMENTS

| | | | |
|---|---|---|---|
| 3,328,419 | 6/1967 | Anderson | 430/558 |
| 3,725,067 | 4/1973 | Bailey et al. | 430/558 |
| 4,548,899 | 10/1985 | Nakayama et al. | 430/558 |
| 4,588,679 | 5/1986 | Furutachi | 430/558 |
| 4,639,413 | 1/1987 | Kawagishi et al. | 430/558 |

Primary Examiner—Richard L. Schilling
Attorney, Agent, or Firm—Connolly & Hutz

[57] ABSTRACT

Color photographic images having advantageous sensitometric properties, in particular high maximum magenta color density, can be obtained by use of a color photographic recording material containing a pyrazoloazole type magenta coupler of formula I $$Q-L-COOH \qquad I$$

In the formula

Q denotes the bicyclic group capable of color coupling in a pyrazolo[3,2-c]-1,2,4-triazole magenta coupler and L denotes a linking member which is not split off in the color coupling reaction and which cointains a ballast residue unless a ballast residue which cannot be split off is attached to the non-coupling ring of the bicyclic group Q.

1 Claim, No Drawings

COLOR PHOTOGRAPHIC RECORDING MATERIAL CONTAINING A COLOR COUPLER OF THE PYRAZOLOAZOLE SERIES

This invention relates to a colour photographic recording material containing at least one silver halide emulsion layer and a colour coupler of the pyrazoloazole series which enables magenta colour images with high colour density to be produced by virtue of the presence of a particular group in the ballast residue.

It is known that coloured photographic images may be produced by chromogenic development, i.e. by developing silver halide emulsion layers which have been exposed imagewise by means of suitable colour producing developer substances, so-called colour developers, in the presence of suitable colour couplers which react with the oxidation product of developer substances formed in areas corresponding to the silver image to produce a dye image. The colour developers used are normally aromatic compounds containing primary amino groups, in particular compounds of the p-phenylenediamine series.

Pyrazolone couplers are normally used for producing magenta dye images. The absorption of the image dyes obtained from these pyrazolone couplers is in many cases not ideal, one particular problem being the yellow side colour density which necessitates the use of masking couplers or other masking techniques if brilliant colours are to be obtained in the photographic image. Other disadvantages commonly found when pyrazolone couplers are used include the inadequate resistance to the action of formaldehyde or the action of light, heat and moisture during storage.

Magenta couplers of the pyrazoloazole series have been found to be preferable in this respect. They generally give rise to magenta dye images with a purer colour but it is difficult to obtain a sufficient colour density with these couplers when the usual methods of processing are employed. Magenta couplers of the pyrazoloazole series are described, for example in DE-A No. 1 810 462, DE-A No. 3 516 996, EP-A No. 0 143 570 and EP-A No. 0 176 804.

It is an object of the present invention to provide a colour photographic recording material containing at least one silver halide emulsion layer and at least one magenta coupler from which magenta dyes with the desired purity of colour and high colour density can be obtained by chromogenic development.

The invention relates to a colour photographic recording material containing at least one silver halide emulsion layer and at least one non-diffusible colour coupler of the pyrazoloazole series, characterised in that the coupler corresponds to the following general formula I

Q—L—COOH    (I)

wherein
Q denotes the bicyclic group capable of colour coupling in a pyrazolo[3,2-c]-1,2,4-triazole magenta coupler and L denotes a linking member which is not split off in the colour coupling reaction and which contains a ballast residue unless a ballast residue which cannot be split off is attached to the non-coupling ring of the bicyclic group Q.

The magenta couplers according to the present invention also correspond to the general formula I-1

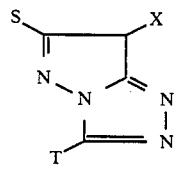 I-1 wherein the substituents S and T may be hydrogen, alkyl, aralkyl, aryl, alkoxy, aroxy, alkylthio, arylthio, amino, anilino, acylamino, cyano, alkoxycarbonyl, carbamoyl or sulphamoyl and these groups may in turn be substituted but at least one of the groups S or T is a group denoted by —L—COOH as defined in formula I. Couplers in which one of the groups S or T is a group L—COOH in which the connecting member L contains a ballast residue are preferred. In formula I-1, X stands for hydrogen or a residue which may be split off in the colour coupling reaction, such as a halogen atom or a group, preferably a cyclic group, which is linked to the coupling position by an oxygen atom, a sulphur atom or a nitrogen atom.

If the releasable group is a cyclic group, it may be attached to the coupling position of the coupler molecule either directly through an atom which forms part of a ring, e.g. a nitrogen atom, or indirectly through a linking member. Many releasable groups of this kind are known, e.g. the fugitive groups of 2-equivalent magenta couplers.

Examples of releasable groups attached to oxygen correspond to the formula

—O—R wherein R denotes an acyclic or cyclic organic group, e.g. alkyl, aryl, a heterocyclic group or acyl, which may be derived, for example, from an organic carboxylic or sulphonic acid. In particularly preferred releasable groups of this kind, R stands for a substituted or unsubstituted phenyl group.

Examples of releasable groups attached through nitrogen are described in the following German Offenlegungsschriften (DE-A-): Nos. 2 536 191, 2 703 589, 2 813 522, 3 339 201.

Many of these groups are 5-membered heterocyclic rings connected to the coupling position of the magenta coupler by a ring nitrogen atom. The heterocyclic rings frequently contain activating groups such as carbonyl or sulphonyl groups or double bonds in positions adjacent to the nitrogen atom through which the rings are attached to the coupling position of the coupler.

If the releasable group is attached to the coupling position of the coupler by a sulphur atom, the group may be a residue of a diffusible carbocyclic or heterocyclic mercapto compound which is capable of inhibiting the development of silver halide. Many such inhibitor groups have been described as releasable groups attached to the coupling position of couplers, including magenta couplers, e.g. in U.S. Pat. No. 3,227,554.

The non-releasable connecting member L attached to a non-coupling position may have a composite structure, for example as represented by the formula:

$$-(L^0)_k-L^1-(L^2)_l-(L^3)_m-(L^4)_n-(L^5)_o-(L^6$$

wherein $L^0$ denotes the part of the connecting member closest to the group Q, and $L^7$ denotes the part of the connecting member closest to the carboxyl group, and $L^0$, $L^2$, $L^4$ and $L^6$, which may be identical or different, denote O, NH, NHCO, CONH, $NHSO_2$ or $SO_2NH$, $L^1$, $L^3$, $L^5$ and $L^7$, which may be identical or different, denote alkylene, aralkylene or arylene, and k, l, m, n, o, p and q each represent 0 or 1 such that $1-m+n-o+p-q=0$, and 1 and m preferably both have the value 1.

An alkylene group denoted by $L^1$, $L^3$, $L^5$ or $L^7$ may be straight chained or branched and may have up to 20 carbon atoms.

An aralkylene group denoted by $L^1$, $L^3$, $L^5$ or $L^7$ may be, for example, one of the following groups:

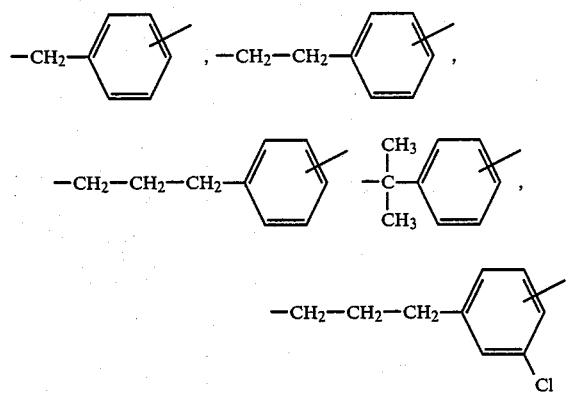

An arylene group denoted by $L^1$, $L^3$, $L^5$ or $L^7$ is preferably a phenylene group which may be substituted, e.g. with alkyl, alkoxy, halogen or acylamino.

The non-releasable connecting member L preferably contains a ballast residue, especially when the noncoupling ring of the pyrazolo[3,2-c]-1,2,4-triazole ring system is not substituted with a ballast residue (different from —L—COOH). If, as is preferred, the non-releasable connecting member L contains a ballast residue, then this residue may consist of the totality of connecting member components $L^1$ to $L^7$ or it may be formed, for example, by one of the connecting member components $L^1$, $L^3$, $L^5$ or $L^7$ containing a ballast residue in the form of a substituent. An alkylene group, for example, may be a 1,2-alkylene group or an alkylidene group with up to 20 carbon atoms; or an arylene group my be substituted, e.g. with an alkoxy group or an acyl-amino group, the said alkoxy group or acylamino group containing up to 20 carbon atoms and/or optionally also containing substituents.

Groups may be regarded as ballast residues if they enable the magenta couplers according to the invention to be incorporated in a diffusion-fast form in the hydrophilic colloids conventionally used in photographic recording materials. These groups are preferably organic groups, generally containing straight chained or branched aliphatic groups with generally 8 to 20 carbon atoms and optionally also containing carbocyclic or heterocyclic, optionally aromatic groups. These ballast residues are attached to the remaining part of the molecule either directly or indirectly, e.g. through one of the following groups: NHCO, $NHSO_2$, NR (wherein R denotes hydrogen or alkyl), O or S. Such a ballast residue may in addition contain groups which confer solubility in water, e.g. hydroxyl groups or carboxyl groups, which may be present in an anionic form. Since the resistance to diffusion depends on the molecular size of the whole compound, it is in some cases sufficient to use ballast residues consisting of several relatively short chained groups. The ballast residues used according to the invention preferably have a molecular weight of less than 1000.

The magenta couplers according to the invention may contain a ballast residue which is not identical to the group —L—COOH. A coupler contains such a ballast residue especially if the group —L—COOH does not itself contain a ballast residue. Such an additional ballast residue may have the structure —L—H in which L has the same meanings as defined for L in L—COOH but always contains a ballast residue.

Examples of pyrazoloazo couplers according to the invention are shown below (Formula I-1):

| coupler (M-) | S | X | T |
|---|---|---|---|
| 1 | —CH₃ | Cl | —(CH₂)₃—O—⟨benzene with C₄H₉-t⟩—NH—CO—CH₂—CH(C₁₈H₃₇)—COOH |
| 2 | —C₄H₉—t | H | —(CH₂)₃—⟨phenyl⟩—NH—CO—⟨phenyl⟩—NH—CO—CH₂—CH(C₁₅H₃₁)—COOH |
| 3 | —CH₃ | Cl | —(CH₂)₃—O—⟨phenyl⟩—NH—SO₂—⟨phenyl⟩—O—CH(C₁₂H₂₅)—COOH |
| 4 | —CH₃ | F | —(CH₂)₃—⟨phenyl⟩—NH—CO—⟨phenyl with OC₁₂H₂₅⟩—COOH |
| 5 | —C₄H₉—t | Cl | —(CH₂)₃—⟨phenyl⟩—NH—CO—⟨phenyl with COOH⟩—NH—CO—C₁₂H₂₅ |
| 6 | —C₄H₉—t | Cl | —(CH₂)₃—⟨phenyl⟩—NH—CO—⟨phenyl⟩—NH—CO—⟨phenyl with COOH⟩ |

-continued

| coupler (M-) | S | X | T |
|---|---|---|---|
| 7 | —CH₃ | 4-COOH-phenoxy | —(CH₂)₃—NH—SO₂—(4-(OC₁₆H₃₃)-3-COOH-phenyl) |
| 8 | —CH₃ | 4-(phenylmethoxy via SO₂)-phenoxy (4-C₆H₅CH₂O–C₆H₄–SO₂–C₆H₄–O–) | —(CH₂)₃—NH—SO₂—(2,5-dimethyl-4-O(CH₂)₃COOH-phenyl) |
| 9 | —CH₃ | succinimido (N-) | —(CH₂)₂—NH—SO₂—(3-Cl-4-O(CH₂)₃COOH-phenyl) |
| 10 | —(CH₂)₃—COOH | Br | —(CH₂)₃—NH—CO—CH(C₁₀H₂₁)—O—(4-(4-HO-phenylsulfonyl)phenyl) |
| 11 | —CH₃ | Cl | —(CH₂)₃—O—(4-[NH—CO—CH(C₁₂H₂₅)-(4-COOH-phenyl)])phenyl ; —C₃H₇ |
| 12 | —(CH₂)₄—NH—SO₂—(4-(OC₁₆H₃₃)-3-COOH-phenyl) | Cl | —C₃H₇ |

-continued

| coupler (M-) | S | X | T |
|---|---|---|---|
| 13 | $-\underset{CH_3}{\underset{|}{CH}}-CH_3$ attached to phenyl ring with $-NH-CO-CH_2-\underset{\underset{C_{16}H_{33}}{|}}{CH}-COOH$ | H | $-C_4H_9$ |
| 14 | $-CH_3$ | H | $-(CH_2)_3-$ phenyl ring with $-NH-CO-CH_2-\underset{\underset{C_{18}H_{37}}{|}}{CH}-COOH$ |

The couplers according to the invention may be synthesized by various methods, e.g. as described in Research Disclosure 12 443 (August 1974):

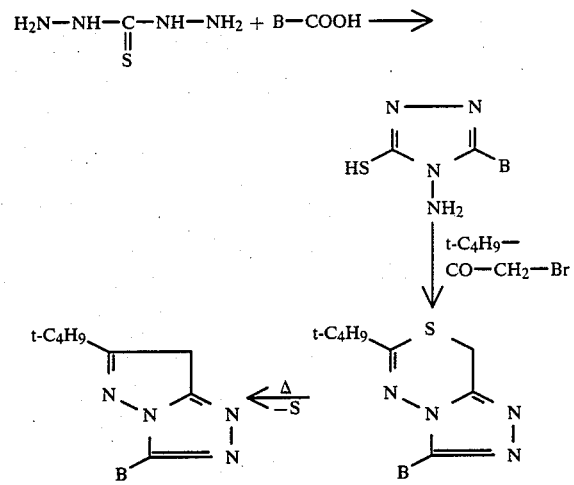

In the above scheme of formulae, B denotes a group —L—COOH or —L—CO—Z wherein Z may be a protective group for the free carboxyl group (e.g. —OC$_2$H$_5$).

Another method of synthesis used, for example, for the coupler M-14 consists of the reaction of 2-[3-(4-aminophenyl)-propyl]-6-methyl-pyrazolo[3,2-c]-1,2,4-triazole with octadecenyl-succinic acid anhydride.

In many cases of synthesizing the couplers according to the invention, it is advantageous for practical reasons of preparation to release the required carboxyl group only in the last stage of the synthesis.

EXAMPLE OF SYNTHESIS 1

Preparation of Coupler M-3 p-Nitrophenoxy-butyric acid chloride was prepared in accordance with the method of synthesis of Coupler 3 given as an example in U.S. Pat. No. 2,865,751. This compound was used instead of p-nitrophenyl-butyric acid chloride to prepare, by the method described in Example 2 of DE-A-No. 3 610 702, under otherwise identical conditions, the compound 3-methyl-4-chloropyrazolone-(5)-N'-ω-4-nitrophenoxy-butyryl-hydrazone from which 7-chloro-6-methyl-3-(p-nitrophenoxypropyl)-1z-H-pyrazolo[3,2-c]-s-triazole was obtained by the method described in Example 4 of DE-A-No. 3 610 702.

1st Stage
300 g of 3-methyl-4-chloropyrazolone-5-hydrazone (75%) were dissolved in
2.3 l of water at 0°°C., and
280 g of sodium acetate followed by
500 ml of methylene chloride were added to the solution. A solution of
500 ml of methylene chloride was added dropwise at 0° C. with rapid stirring within 2 hours.
Stirring was continued for 30 minutes and the reaction mixture was then suction filtered and washed with a large quantity of water, and the product was dried at 50° C.
Yield: 286 g=84% of theoretical.
M.pt. 155°-158° C.
The proportion of product present was determined by titration with tetrabutyl ammonium hydroxide and found to be 99%.

2nd Stage
143 g of the acylhydrazone obtained as described above were heated to 50°-60° C. in
540 ml of Sulpholan, and
145 ml of phosphorus oxychloride were added within 1-2 minutes while the acylhydrazone was heated. Complete solution occurred at 90° C. and stirring was then continued for 30 minutes at 115°-120° C. After cooling,
2500 ml of water were stirred in and stirring was continued for 1 hour. The product was then suction filtered, suspended in ethanol and stirred for 15 minutes.
Yield: 198 g=72% of theoretical
M.pt. 188°-189° C.

3rd Stage
256 g of 7-chloro-6-methyl-3-(p-nitrophenoxypropyl)-1-H-pyrazolo[3,2-c]-s-triazole obtained as product in Stage 2 were heated to boiling with
256 g of Fe powder in
2560 ml of methanol.
256 ml of concentrated hydrochloric acid were then added dropwise within 20 minutes. The starting product then completely dissolved.
100 ml of concentrated hydrochloric acid were subsequently added and when the reaction was completed the iron was removed by suction filtration. The filtrate was precipitated into ice/water, suction filtered, washed and dried.
Yield: 165 g=93% of theoretical
M.pt.: 172°-175° C. with decomposition.

4th Stage
120 g of 7-Chloro-6-methyl-3-(p-aminophenoxypropyl)-1-H-pyrazolo[3,2-c]-s-triazole were dissolved or suspended in
900 ml of dioxane, and
200 ml of pyridine were then added.
215 g of α-(4-chlorosulphonylphenoxy)-myristic acid ethyl ester were added dropwise at room temperature.
After completion of the reaction, the product was stirred into ice/HCl, taken up in ethyl acetate and separated. The solution in ethyl acetate was treated with Fuller's earth and freed from solvent under vacuum. The coupler M-3 crystallised towards the end. Recrystallisation from acetonitrile.
Yield: 199 g=70% of theoretical.
M.pt. 75° C.
The product was again dissolved in ethanol and hydrolysed with half concentrated sodium hydroxide solution. The product obtained after reprecipitation in ice/-hydrochloric acid was recrystallised twice from methanol with active charcoal.
Yield: 175 g
M.pt.: 50°-55° C.

Apart from the advantageous spectral properties of the image dyes produced from them and the excellent stability of the emulsions, the couplers according to the invention are particularly distinguished by the fact that the dyes obtained from them by the conventional process of colour development are produced with a high colour yield so that high maximum colour densities are obtained. Furthermore, the coupling activity of these couplers is comparatively unaffected by fluctuations in the pH of the developer solution, in particular by the sometimes unavoidable lowering of the pH. This is particularly advantageous for the sensitometric properties of the colour photographic recording material.

For the preparation of light-sensitive colour photographic recording materials, the diffusion-resistant couplers according to the present invention may be incorporated in a known manner in the casting solution for the silver halide emulsion layers or for other colloid layers. Oil soluble or hydrophobic couplers, for example, may advantageously be added to a hydrophilic colloid solution from a solution in a suitable coupler solvent (oil former), optionally in the presence of a wetting or dispersing agent. The hydrophilic casting solution may, of course, contain the usual additives in addition to the binder. The solution of coupler need not be directly dispersed in the casting solution for the silver halide emulsion layer or other water-permeable layer but may advantageously first be dispersed in an aqueous, light-insensitive solution of a hydrophilic colloid and the resulting mixture may then be added to the casting solution for the light-sensitive silver halide emulsion layer or other water-permeable layer, the low boiling organic solvent used being first removed if necessary, and the resulting mixture may then be cast.

The light-sensitive silver halide emulsions used may be emulsions of silver chloride, silver bromide or mixtures thereof, optionally with a small silver iodide content of up to 10 mol-%, in one of the conventionally used hydrophilic binders. The binder used for the photographic layers is preferably gelatine although this may be partly or completely replaced by other natural or synthetic binders.

The emulsions may be chemically or spectrally sensitized in the usual manner and the layers of emulsion as well as other, light-insensitive layers may be hardened in the usual manner with known hardeners, in particular with hardeners containing compounds which activate carboxyl groups, such as carbamoyl pyridinium salts (e.g. according to DE-A No. 22 25 230, DE-A No. 23 17 677, DE-A No. 24 39 551).

Colour photographic recording materials normally contain at least one silver halide emulsion layer for recording light from each of the three spectral regions, red, green and blue. The light-sensitive layers are spectrally sensitized for this purpose by means of suitable sensitizing dyes in a known manner. Blue-sensitive silver halide emulsion layers need not necessarily contain a spectral sensitizer since the intrinsic sensitivity of the silver halide is in many cases sufficient for recording blue light.

Each of the above-mentioned light-sensitive layers may consist of a single layer or it may be composed of two or more silver halide emulsion partial layers in a known manner, for example as in the so-called double layer arrangement (DE-C-1 121 470). Red-sensitive silver halide emulsion layers are normally arranged closer to the layer support than green-sensitive silver halide emulsion layers, which in turn are arranged closer to the layer support than blue-sensitive layers, and the blue-sensitive and green-sensitive layers are generally separated by a light-insensitive yellow filter layer, although other arrangements could be used. A light-insensitive interlayer is generally provided between layers which differ in their spectral sensitivity. This interlayer may contain means for preventing accidental diffusion of developer oxidation products. If several silver halide emulsion layers of the same spectral sensitivity are provided, these may be arranged directly adjacent to one another or they may be separated by a light-sensitive layer having a different spectral sensitivity (DE-A No. 1 958 709, DE-A No. 2 530 645, DE-A No. 2 622 922.

Colour photographic recording materials for the production of multicolour images by chromogenic development normally contain non-diffusible colour couplers arranged in spatial and spectral association with the silver halide emulsion layers of the various spectral sensitivities to produce partial colour images in cyan, magenta and yellow.

The term "spatial association" is used to denote that the colour coupler is situated in such a spatial relationship to the silver halide emulsion layer that the coupler and the layer are capable of interacting to give rise to an imagewise correspondence between the silver image formed on development and the colour image produced from the colour coupler. This is generally achieved by arranging the colour coupler in the silver halide emulsion layer or in an adjacent layer of binder which may be insensitive to light.

The term "spectral association" is used to denote that the spectral sensitivity of each of the lightsensitive silver halide emulsion layers and the colour of the partial colour image produced from the spatially associated colour coupler are in a certain relationship to one another, each of the spectral sensitivities (red, green, blue) being associated with a partial colour image of a different colour (generally, for example, the colours cyan, magenta and yellow, in this sequence).

Each of the silver halide emulsion layers sensitized to different regions of the spectrum may be associated with one or more colour couplers. If the photographic material contains several silver halide emulsion layers having the same spectral sensitivity, each of these layers may contain a colour coupler and the colour couplers need not necessarily be identical, provided only that on colour development they give rise to at least approximately the same colour, normally a colour which is complementary to the colour of the light to which the particular silver halide emulsion layers are predominantly sensitive.

In the preferred embodiments, therefore, red-sensitive silver halide emulsions are associated with at least one non-diffusible colour coupler for producing the cyan partial colour image, generally a coupler of the phenol or α-naphthol series; green-sensitive silver halide emulsion layers are associated with at least one non-diffusible colour coupler for the production of the magenta partial colour image, in the present case a colour coupler corresponding to formula I; lastly, blue-sensitive silver halide emulsion layers are associated with at least one non-diffusible colour coupler for production of the yellow partial colour image, generally a colour coupler containing an open chain keto methylene group. Many colour couplers of this kind are known and have been described in numerous Patent Specifications and other documents; see, for example, the publication entitled "Farbkuppler" by W. Pelz in "Mitteilungen aus den Forschungslaboratorien der Agfa, Leverkusen/Me,uml/u/ unchen", Volume III, page 111 (1961) and the publication by K. Venkataraman in "The Chemistry of Synthetic Dyes", Vol. 4, 341 to 387, Academic Press (1971).

The colour couplers may be 4-equivalent couplers or they may be 2-equivalent couplers. The latter are derived, as is known from 4-equivalent couplers in that they contain, in the coupling position, a substituent which is released in the coupling reaction. The 2-equivalent couplers include both those which are virtually colourless and those which have an intense colour of their own which disappears in the process of colour coupling and may be replaced by the colour of the image dye produced (masking couplers). The known white couplers are in principle also 2-equivalent couplers although they give rise to substantially colourless products in their reaction with colour developer oxidation products. Also to be included among the 2-equivalent couplers are those couplers which carry in the coupling position a group which is released in the reaction with colour developer oxidation products to develop a certain photographic activity, e.g. as development inhibitor or accelerator, either directly or after removal of one or more further groups from the group originally released (e.g. DE-A No. 2 703 145, DE-A No. 2 855 697, DE-A No. 3 105 026 and DE-A No. 3 319 428). Examples of such 2-equivalent couplers include the known DIR couplers as well as DAR and FAR couplers.

Suitable DIR couplers are described, for example, in GB-A No. 953 454, DE-A No. 1 800 420, DE-A No. 2 015 867, DE-A No. 2 414 006, DE-A No. 2 842 063 and DE-A No. 3 427 235.

Suitable DAR couplers and FAR couplers are described, for example, in GB-A No. 1 591 641, DE-A No. 3 209 110, EP-A No. 0 089 834, EP-A No. 0 117 511 and EP-A No. 0 118 087.

Since the DIR, DAR and FAR couplers are used mainly because of the activity of the group released in the coupling reaction and the colour producing properties of these couplers is less important, those DIR, DAR and FAR couplers which give rise to substantially colourless products in the coupling reaction are also suitable, for example those described in DE-A No. 1 547 640.

The releasable group may be a ballast residue so that the reaction with colour developer oxidation products may give rise to coupling products, e.g. dyes which are diffusible or at least have a certain, limited mobility, for example as described in U.S. Pat. No. 4,420,556.

High molecular weight colour couplers are described, for example, in DE-C No. 1 297 417, DE-A No. 2 407 569, DE-A No. 3 148 125, DE-A No. 3 217 200, DE-A No. 3 320 079, DE-A No. 3 324 932, DE-A No. 3 331 743, DE-A No. 3 340 376, EP-A No. 27 284 and U.S. Pat. No. 4,080,211. The high molecular weight colour couplers are generally prepared by the polymerisation of ethylenically unsaturated, monomeric colour couplers although they may be obtained by polyaddition or polycondensation reactions.

According to the present invention, the colour photographic recording material contains at least one coupler having the structure corresponding to formula I. The advantages achieved with such a coupler may be seen from the examples described below. Although the exact relationships are not known in detail, it is assumed that the advantages obtained with the couplers according to the invention are due to the structure of the couplers illustrated in formula I, in particular the special structure of the —L—COOH group.

The characteristic group of the couplers of formula I has no major influence on the spectral properties of the image dyes produced but the carboxyl group has an advantageous effect on the maximum colour density obtainable and the stability to fluctuations in the pH of the colour developer solution.

In addition to the components already mentioned, the photographic recording material according to the present invention may contain additives such as, for example, anti-oxidants, dye stabilizers and substances influencing the mechanical and electrostatic properties. It is advantageous, for example, to use UV absorbent compounds in one or more of the layers of the recording material, preferably one of the upper layers, for the purpose of preventing or reducing the adverse effect of UV light on the colour images produced with the colour photographic recording material according to the invention. Suitable UV absorbents are described, for example, in U.S. Pat. No. 3,253,921, DE-C No. 2 036 719 and EP-A No. 0 057 160.

For the production of colour photographic images, the colour photographic recording material according to the invention, which contains at least one silver halide emulsion layer and at least one coupler of formula I associated with this layer, is developed with a colour developer compound. The colour developer compound used may be any developer compound whose oxidation product is capable of reacting with colour couplers to form azomethine dyes. Suitable colour developer compounds include aromatic compounds of the p-phenylenediamine series containing at least one primary amino group; for example, N,N-dialkyl-p-phenylenediamines such as N,N-diethyl-p-phenylenediamine, 1-(N-ethyl-N-methyl-sulphonamidoethyl)-3-methyl-p-phenylenediamine, 1-(N-ethyl-N-hydroxyethyl)-3-methyl-p-phenylenediamine and 1-(N-ethyl-N-methoxyethyl)-3-methyl-p-phenylenediamine.

Other suitable colour developers are described, for example, in J.Amer.Chem.Soc. 73, 3100 (1951) and in Modern Photographic Processing by G. Haist, 1979, John Wiley and Sons, New York, pages 545 et seq.

After colour development, the material is bleached and fixed in the usual manner. Bleaching and fixing may be carried out separately or together. The usual bleaching compounds may be used, e.g. $Fe^{3+}$ salts and $Fe^{3+}$ complex salts such as ferricyanides, dichromates, water-soluble cobalt complexes, etc. Iron-III complexes of amino-polycarboxylic acids are especially preferred, e.g. the complexes of ethylene diaminotetracetic acid, of N-hydroxyethyl-ethylene-diaminotriacetic acid, of alkyliminodicarboxylic acids and of the corresponding phosphonic acids. Persulphates are also suitable bleaching agents.

EXAMPLE 1

8 mmol of each magenta coupler were dissolved in ethyl acetate (EA) at about 50° C. in proportions of 1:3 and dibutylphthalate (DBP) and a wetting agent (di-n-octyl sulfosuccinate) were added so that the components were present in the following proportions:

Coupler : DBP : EA : wetting agent = 1:1:3:=0.1.

The mixture was then emulsified in 7.5% gelatine solution and the emulsion was stirred at 1000 revs/min for 6 minutes, during which it heated up to about 50° C. EA was removed by suction filtration in a water jet vacuum (200–300 mbar). The emulsions prepared as described above were mixed with a silver iodobromide emulsion (0.7 mol-% iodide) in proportions of 1 mol of coupler to 5.2 mol of $AgNO_3$, and each mixture was applied to a layer support of cellulose acetate and covered wtih a protective layer of a 3% gelatine solution containing carbamoyl pyridinium betaine (CAS Reg. No. 65411-60-1) as hardener. The samples were dried and cut up and then exposed behind a step wedge and processed by the negative-AP 70 process (38° C.).

| Bath | min |
|---|---|
| Colour developer (CD 70) | 3.25 |
| Bleaching bath | 6.5 |
| Washing | 3.0 |
| Fixing bath | 6.5 |
| Washing | 6.0. |

The following baths were used:
Colour developer
  8000 ml water
  17 g sodium hydroxyethane diphosphonate
  12 g ethylene diaminotetracetic acid (EDTA acid)
  47 g 1-(N-ethyl-N-hydroxyethyl)-3-methyl-p-phenylene diamine
  25 g hydroxylammonium sulphate
  39 g sodium sulphite
  15.5 g sodium bicarbonate
  335 g potassium carbonate
  13.5 g potassium bromide made up with water to 10 l; pH 10.0
Bleaching bath
  8000 ml water
  1390 g ammonium bromide
  865 g EDTA $NH_4$-Fe
  163 g EDTA acid
  100 g ammonia made up with water to 10 l and adjusted to pH 6.0 ±0.1 with about 15 ml glacial acetic acid
Fixing bath
  8000 ml water
  1500 g ammonium thiosulphate
  100 g sodium sulphite
  20 g sodium hexametaphosphate made up with water to 10 l; pH 7.5

Further developments were carried out with the only difference that the colour developer bath was adjusted to a pH value of 9.6, 9.8, 10.2 and 10.4, respectively. The maximum magenta colour densities obtained are shown in Table 1.

TABLE 1

| Coupler | pH: | $D_{max}$ at the following pH of colour developer: | | | | |
|---|---|---|---|---|---|---|
| | | 9.6 | 9.8 | 10.0 | 10.2 | 10.4 |
| COUP 1 | | 0.31 | 0.5 | 1.02 | 1.58 | 1.64 |
| COUP 2 | Comparison | 0.54 | 0.62 | 1.52 | 1.70 | 1.84 |
| COUP 3 | | 0.32 | 0.71 | 1.38 | 1.84 | 1.84 |
| COUP 4 | | 0.40 | 0.48 | 1.22 | 1.68 | 1.70 |
| M-3 | | 0.80 | 1.85 | 2.00 | 2.64 | 2.66 |
| M-4 | according to | 0.68 | 1.96 | 2.22 | 2.84 | 2.90 |
| M-11 | the invention | 0.95 | 2.10 | 2.58 | 2.80 | 2.82 |
| M-14 | | 1.20 | 2.20 | 2.60 | 2.94 | 2.92 |

The following couplers were used for comparison:

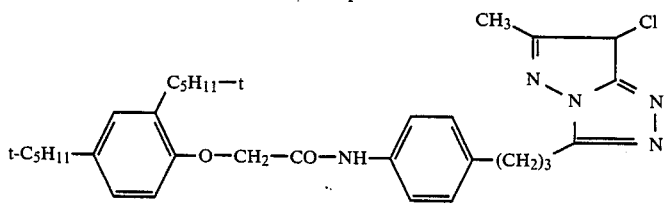

Coup 1

TABLE 1-continued
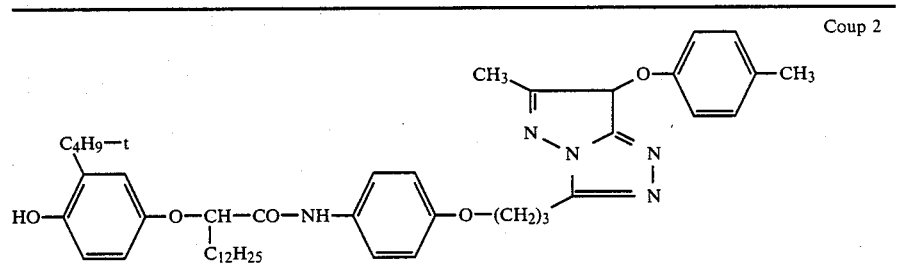
Coup 2
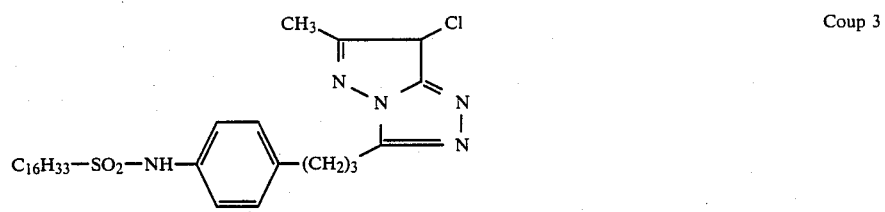
Coup 3
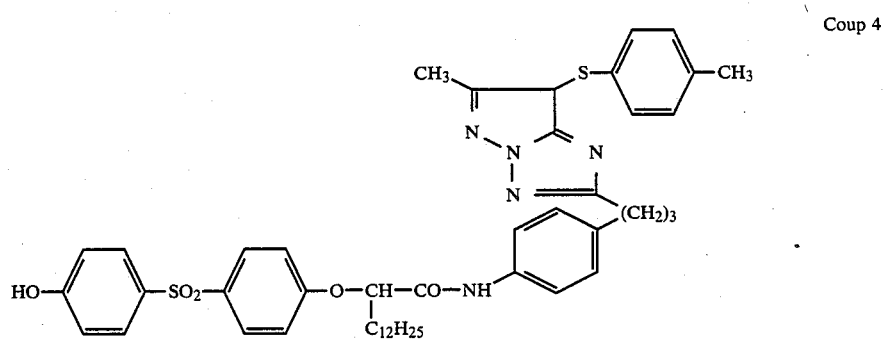
Coup 4
EXAMPLE 2
Further samples of colour photographic recording materials were prepared and processed as described in Example 1, using the couplers mentioned in Table 2 (Coupler according to the invention and Comparison Couplers).
The following Comparison couplers were used:
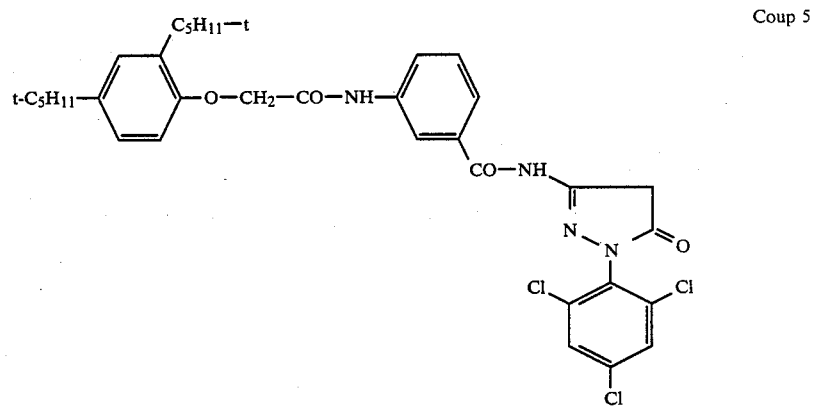
Coup 5
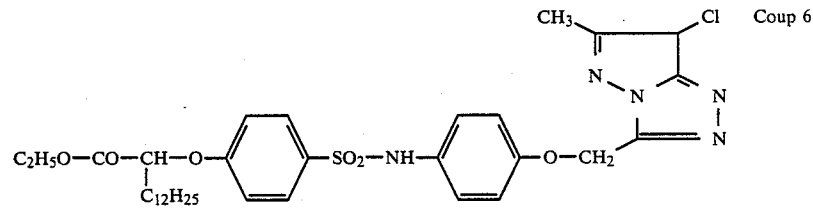
Coup 6

Coup 7

Coup 8

The results of photographic sensitivity E, gradation γ, colour yield FA and fog S are shown in Table 2.

TABLE 2

| Coupler | E | γ | FA | S |
|---|---|---|---|---|
| COUP 5 | standard | 0.6 | 1.40 | 0.13 |
| COUP 6 | −0.6 | 0.42 | 1.60 | 0.12 |
| COUP 7 | −2.5 | 0.68 | 1.82 | 0.10 |
| COUP 8 | +0.6 | 0.48 | 2.0 | 0.18 |
| M-6 | +3.0 | 1.04 | 2.82 | 0.12 |

EXAMPLE 3

A colour photographic recording material for negative colour development was prepared by applying the following layers in the given sequence to a transparent layer support of cellulose triacetate. The quantities are based in each case on 1 m². The quantities of silver halide applied are given in the corresponding quantities of AgNO₃. All the silver halide emulsions were stabilized with 0.5 g of 4-hydroxy-6-methyl-1,3,3a,7-tetraazaindene per 100 g.

Layer 1 (Antihalation layer)
  Black colloidal silver sol containing
  0.18 g Ag
  0.30 g UV absorbent UV-1 and
  1.5 g gelatine
Layer 2 (Interlayer)
  Silver iodobromide emulsion (0.8 mol-% iodide) obtained from 0.15 g AgNO₃ with
  0.15 g 2,5-dioctylhydroquinone
  0.11 g coupler C-1 and
  0.3 g gelatine
Layer 3 (1st red-sensitized layer)
  Red-sensitized silver iodobromide emulsion
  (5 mol-% iodide) obtained from 0.7 g
  AgNO₃ with
  0.1 g Coupler C-2,
  0.3 g Coupler C-3,
  0.01 g Coupler C-4 and
  1.2 g gelatine
Layer 4 (2nd red-sensitized layer)
  Red-sensitized silver iodobromide emulsion
  (10 mol-% iodide) obtained from 1.2 g
  AgNO₃ with
  0.1 g Coupler C-2,
  0.05 g Coupler C-3,
  0.05 g Coupler C-5 and
  0.9 g gelatine
Layer 5 (3rd red-sensitized layer)
  Red-sensitized silver iodobromide emulsion
  (10 mol-% iodide) obtained from 2.0 g
  AgNO₃ with
  0.05 g Coupler C-3,
  0.15 g Coupler C-5,
  0.003 g Coupler C-6 and
  0.8 g gelatine
Layer 6 (Interlayer)
  0.5 g gelatine
Layer 7 (1st green-sensitized layer)
  Green sensitized silver iodobromide emulsion
  (5 mol-% iodide) obtained from 0.5 g AgNO₃
  with
  0.3 g Coupler C-7,
  0.4 g Coupler C-8,
  0.5 g Coupler C-9,
  0.5 g Coupler C-10 and
  1.2 g gelatine
Layer 8 (2nd green-sensitized layer)
  Green-sensitized silver iodobromide emulsion
  (6 mol-% iodide) obtained from 1.0 g AgNO₃
  with
  0.25 g Coupler C-7,
  0.01 g Coupler C-8,
  0.01 g Coupler C-9,
  0.01 g Coupler C-10 and
  1.7 g gelatine
Layer 9 (3rd green-sensitive layer)
  Green-sensitized silver iodobromide emulsion
  (10 mol-% iodide) obtained from 1.5 g
  AgNO₃ with
  0.015 g Coupler C-8,
  0.07 g Coupler C-11,
  0.002 g Coupler C-12 and
  1.0 g gelatine
Layer 10 (Yellow filter layer)
  Yellow colloidal silver sol obtained from
  0.05 g Ag with
  0.03 g 3,5-ditert.-octylhydroquinone and
  0.6 g gelatine
Layer 11 (1st Blue-sensitive layer)
  Silver iodobromide emulsion (5 mol-% iodide)
  obtained from 0.3 g AgNO₃ with
  0.7 g Coupler C-13, 0.03 g Coupler C-14 and
1.4 g gelatine Layer 12 (2nd blue-sensitive layer)
Silver iodobromide emulsion (5 mol-% iodide) obtained from 0.3 g AgNO$_3$ with
0.25 g Coupler C-13 and
0.6 g gelatine Layer 13 (Micrate layer)
Silver iodobromide emulsion (2 mol-% iodide) obtained from 0.4 g AgNO$_3$ with
0.1 g gelatine Layer 14 (3rd blue-sensitive layer)
Silver iodobromide emulsion (10 mol-% iodide) obtained from 0.8 g AgNO$_3$ with
0.2 g Coupler C-13 and
0.5 g gelatine Layer 15 (1st protective layer)
0.14 g UV absorbent UV-1,
0.20 g UV absorbent UV-2 and
0.4 g gelatine Layer 16 (2nd protective layer)
0.95 g of hardener CAS Reg. No. 65411-60-1 and
0.23 g gelatine.

The recording material prepared as described above will be referred to as Material A (not according to the invention). A material B conforming to the present invention was prepared by the same method. This Material B differed from Material A only in that layers 7, 8, and 9 contained the couplers M-3 and M-11 instead of couplers C-7 and C-11.

The following sensitometric data (Table 3) were obtained after exposure and processing as described in Example 1:

TABLE 3

| Material | Coupler | E | $D_{max}$ | $\gamma$ | $\lambda_{max}$ | S |
|---|---|---|---|---|---|---|
| A | C-7/C-11 | ±0 (standard) | 2.2 | 0.8 | 555 | 0.12 |
| B | M-3/M-11 | +1.8 | 3.3 | 1.42 | 553 | 0.12 |

The following $D_{max}$ values (Table 4) are obtained after exposure and processing if the materials A and B are exposed to a formalin concentration of 10 ppm at 70% relative humidity for 0, 3, 7, 14 or 21 days prior to exposure:

TABLE 4

| Material | Coupler | $D_{max}$ Days: 0 | 3 | 7 | 14 | 21 |
|---|---|---|---|---|---|---|
| A | C-7/C-11 | 2.2 | 2.2 | 1.9 | 1.5 | 1.0 |
| B | M-3/M-11 | 3.3 | 3.2 | 3.08 | 3.08 | 3.0 |

The following compounds were used:

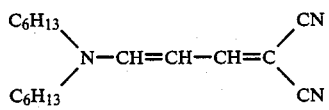

UV-1

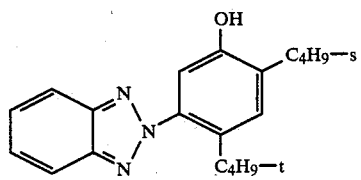

UV-2

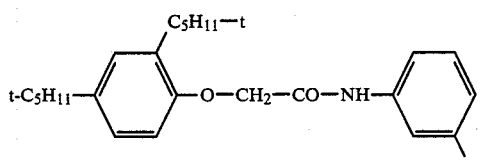

C-1

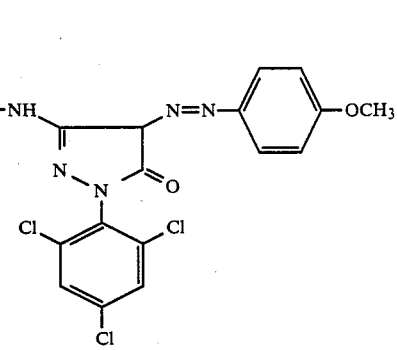

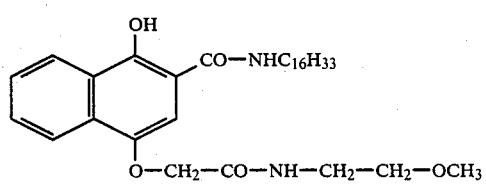

C-2

-continued
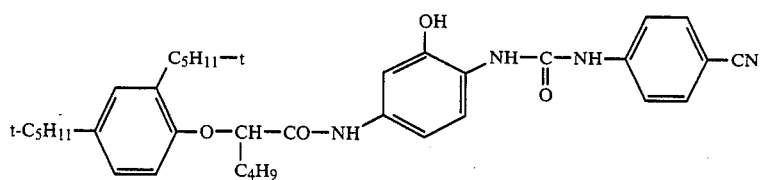
C-3
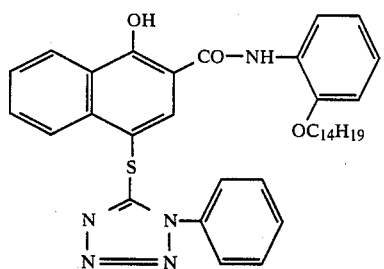
C-4
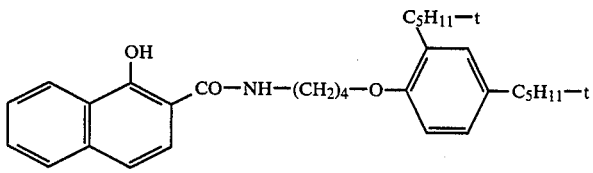
C-5
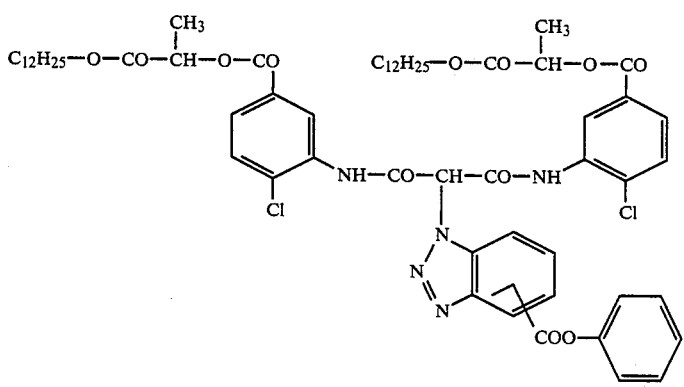
C-6
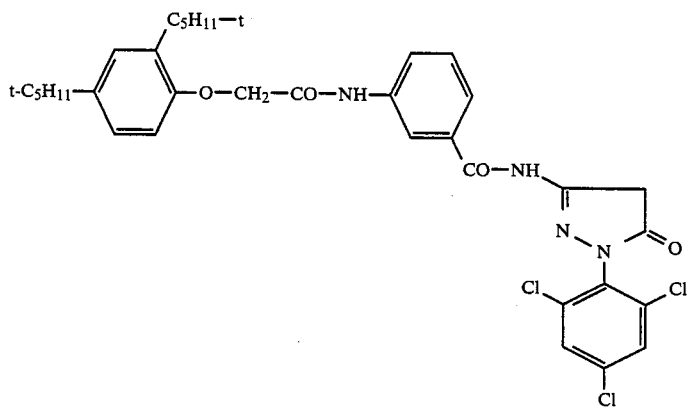
C-7

-continued
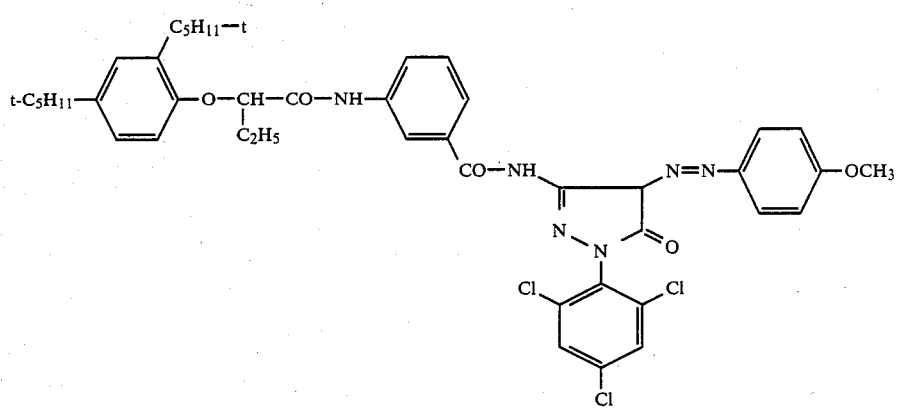
C-8
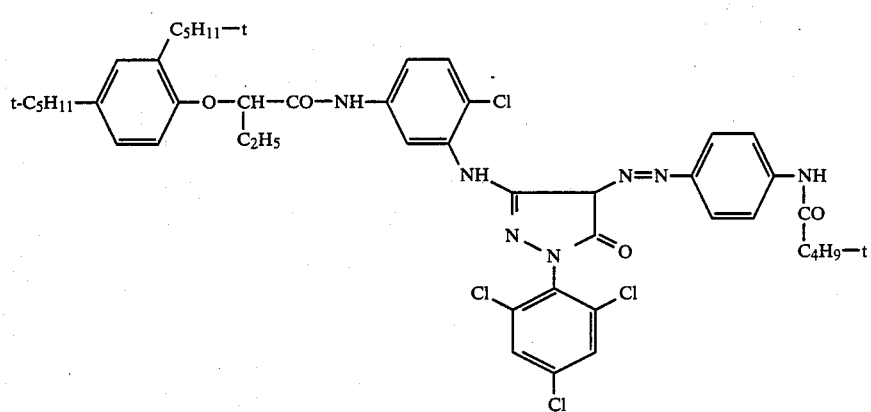
C-9
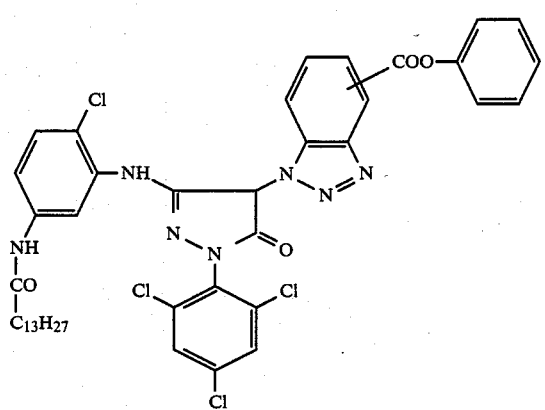
C-10
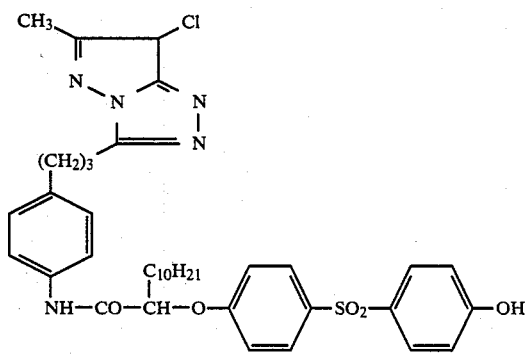
C-11

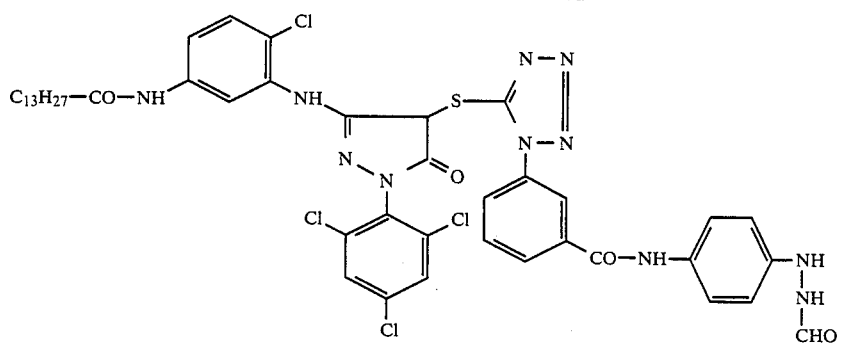
C-12

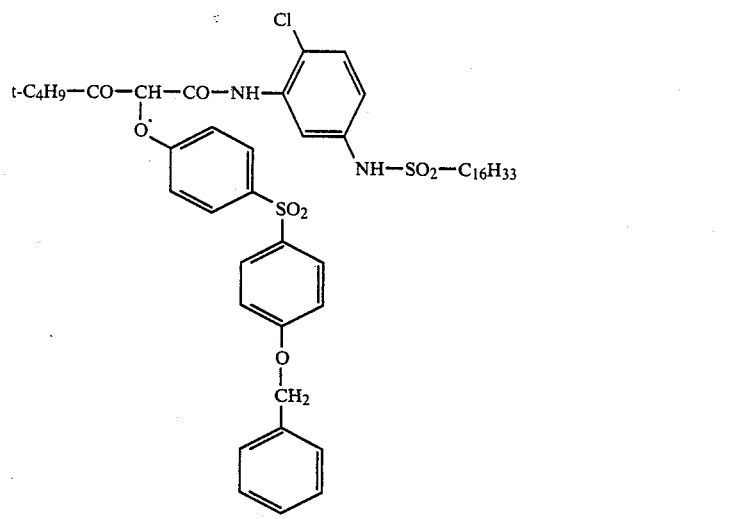
C-13

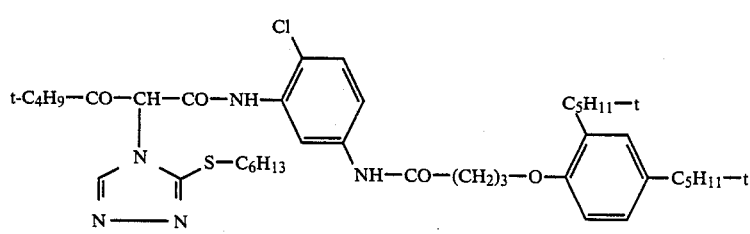
C-14

We claim:

1. Color photographic recording material containing at least one silver halide emulsion layer and at least one nondiffusible color coupler of the pyrazolo[3,2-c]-1,2,4-triazole magenta coupler series, wherein the color coupler corresponds to the following formula I-1

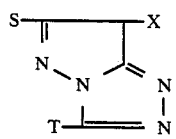
I-1 wherein S and T denote hydrogen, alkyl, aralkyl, aryl, alkoxy, aroxy, alkylthio, arylthio, amino, anilino, acylamino, cyano, alkoxycarbonyl, carbamoyl or sulfamoyl and X denotes hydrogen or a residue which can be split off in the color coupling reaction provided that at least one of S and T represents a group of the following structure:

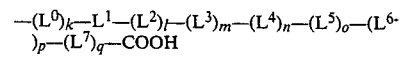

wherein the various groups have the following meaning (identical or different):

$L^0$, $L^2$, $L^4$, $L^6$: —O—, —NH—, —NHCO—, —CONH—, —NHSO$_2$—, —SO$_2$NH—;

$L^1$, $L^3$, $L^5$, $L^7$: alkylene with up to 20 carbon atoms, aralkylene, arylene; and k,l,m,n,o,p and q each have the value 0 or 1 and $1-m+n-o+p-q=0$;

at least one of $L^1$, $L^3$, $L^5$ and $L^7$ also containing a ballast residue unless a ballast residue is contained in T.

* * * * *

UNITED STATES PATENT AND TRADEMARK OFFICE
CERTIFICATE OF CORRECTION

PATENT NO. : 4,835,094
DATED : May 30, 1989
INVENTOR(S) : Wolff et al.

It is certified that error appears in the above-identified patent and that said Letters Patent is hereby corrected as shown below:

Col. 3, line 10, insert -- $)_p-(L^7)_q$ -- after "$-(L^5)_o-(L^6$".

Col. 11, line 52, "-1z-H" should read -- -1-H --.

Col. 15, line 13, "Me,uml/u/unchen" should read -- Muenchen --.

In Claim 1, Col. 30, lines 50 and 51, please show the total of the group represented by one of S and T in one line, as follows:

-- $-(L^0)_k-L^1-(L^2)_l-(L^3)_m-(L^4)_n-(L^5)_o-(L^6)_p-(L^7)_q-COOH$ --.

Signed and Sealed this

Twenty-sixth Day of June, 1990

*Attest:*

HARRY F. MANBECK, JR.

*Attesting Officer*     *Commissioner of Patents and Trademarks*